United States Patent
Lefebvre

(10) Patent No.: US 7,288,228 B2
(45) Date of Patent: Oct. 30, 2007

(54) SAMPLE INJECTION SYSTEM

(75) Inventor: Paul M. Lefebvre, Cumberland, RI (US)

(73) Assignee: Gilson, Inc., Middleton, WI (US)

( * ) Notice: Subject to any disclaimer, the term of this patent is extended or adjusted under 35 U.S.C. 154(b) by 746 days.

(21) Appl. No.: 10/075,811

(22) Filed: Feb. 12, 2002

(65) Prior Publication Data

US 2003/0152493 A1    Aug. 14, 2003

(51) Int. Cl.
  *B01L 3/02* (2006.01)
  *G01N 30/16* (2006.01)
  *G01N 1/10* (2006.01)
  *G01N 1/14* (2006.01)

(52) U.S. Cl. .......................... 422/100; 422/63; 422/67; 422/70; 436/180; 73/864; 73/864.12; 73/864.15

(58) Field of Classification Search ................ 422/100, 422/103, 63, 70; 436/180; 73/863.32, 863.41, 73/863.44, 863.72, 863.83, 863.86, 864, 73/864.01, 864.12, 864.15
See application file for complete search history.

(56) References Cited

U.S. PATENT DOCUMENTS

| | | | |
|---|---|---|---|
| 3,858,450 A * | 1/1975 | Jones ........................ | 73/863.72 |
| 4,326,837 A | 4/1982 | Gilson et al. | |
| 4,347,215 A * | 8/1982 | Sisti et al. ..................... | 422/63 |
| 4,422,151 A | 12/1983 | Gilson | |
| 4,517,302 A * | 5/1985 | Saros ......................... | 436/180 |
| 4,705,668 A * | 11/1987 | Kaltenbach et al. .......... | 422/82 |
| 4,957,009 A * | 9/1990 | Nohl et al. ............... | 73/864.84 |
| 5,094,961 A * | 3/1992 | del Valle et al. ............. | 436/180 |
| 5,158,748 A * | 10/1992 | Obi et al. .................... | 422/100 |
| 5,189,919 A * | 3/1993 | Hernandez ................ | 73/863.43 |
| 5,277,871 A * | 1/1994 | Fujii et al. ..................... | 422/70 |
| 5,306,510 A * | 4/1994 | Meltzer ........................ | 422/65 |
| 5,312,757 A * | 5/1994 | Matsuyama et al. .......... | 436/54 |
| 5,483,843 A * | 1/1996 | Miller et al. ............. | 73/864.23 |
| 5,593,893 A * | 1/1997 | Kobashi et al. ................ | 436/50 |
| 5,820,824 A * | 10/1998 | Tanaka ........................ | 422/100 |
| 5,904,899 A * | 5/1999 | Hayashi ........................ | 422/65 |
| 6,045,755 A * | 4/2000 | Lebl et al. ..................... | 422/65 |
| 6,143,573 A * | 11/2000 | Rao et al. .................... | 436/180 |
| 6,158,269 A * | 12/2000 | Dorenkott et al. ............. | 73/37 |
| 6,190,614 B1 * | 2/2001 | Fukunaga .................... | 422/100 |
| 6,241,947 B1 * | 6/2001 | Komatsu et al. .............. | 422/67 |
| 6,265,226 B1 * | 7/2001 | Petro et al. .................. | 436/180 |
| 6,355,164 B1 * | 3/2002 | Wendell et al. .......... | 210/198.2 |
| 6,537,505 B1 * | 3/2003 | LaBudde et al. ........... | 422/103 |

(Continued)

FOREIGN PATENT DOCUMENTS

EP    0 990 899    5/1998

(Continued)

OTHER PUBLICATIONS

Gilson Product Guide 2000; Feb. 2000; pp. 8 & 30.

*Primary Examiner*—Brian R. Gordon
(74) *Attorney, Agent, or Firm*—Foley & Lardner LLP

(57) ABSTRACT

An HPLC injection valve is mounted to a probe drive system close to the probe axis to minimize probe movements required for sample injections into a mobile phase column. The probe is directly connected by a short conduit to the injection valve, eliminating the need to dispense aspirated samples from the probe into a remote injection port.

20 Claims, 2 Drawing Sheets

U.S. PATENT DOCUMENTS

| | | | |
|---|---|---|---|
| 6,551,557 B1* | 4/2003 | Rose et al. | 422/100 |
| 6,551,839 B2* | 4/2003 | Jovanovich et al. | 436/180 |
| 6,589,791 B1* | 7/2003 | LaBudde et al. | 436/55 |
| 6,592,825 B2* | 7/2003 | Pelc et al. | 422/100 |
| 6,656,724 B1* | 12/2003 | Heimberg et al. | 435/286.4 |
| 6,743,397 B1* | 6/2004 | Zesiger | 422/67 |
| 2001/0010936 A1* | 8/2001 | Richards et al. | 436/49 |
| 2001/0016177 A1* | 8/2001 | Pelc et al. | 422/100 |
| 2002/0006356 A1* | 1/2002 | Neal et al. | 422/63 |
| 2002/0106813 A1* | 8/2002 | Smith et al. | 436/180 |
| 2002/0127146 A1* | 9/2002 | Bergh et al. | 422/89 |
| 2002/0159919 A1* | 10/2002 | Churchill et al. | 422/100 |
| 2002/0168297 A1* | 11/2002 | Shvets et al. | 422/100 |
| 2002/0192113 A1* | 12/2002 | Uffenheimer et al. | 422/67 |
| 2003/0062265 A1* | 4/2003 | King et al. | 204/453 |
| 2003/0099573 A1* | 5/2003 | Tseung et al. | 422/63 |
| 2003/0170903 A1* | 9/2003 | Johnson et al. | 436/100 |
| 2003/0215957 A1* | 11/2003 | Lemmo et al. | 436/180 |
| 2005/0032242 A1* | 2/2005 | Sasaki | 436/180 |

FOREIGN PATENT DOCUMENTS

| | | |
|---|---|---|
| JP | 62050659 | 3/1987 |

* cited by examiner

SAMPLE INJECTION SYSTEM

FIELD OF THE INVENTION

The present invention relates to sample handling and more particularly to a high throughput sample injection system for liquid sample analysis systems such as liquid chromatography.

DESCRIPTION OF THE PRIOR ART

In performing high pressure liquid chromatography, samples are injected into a mobile phase that is supplied to a sample analysis assembly such as a chromatography column and detector. In order to automate the process and to achieve high sample throughput, an automated liquid handler may be used for supplying the samples in a predetermined sequence. In a known sample injection system, each sample is aspirated with a probe from one of an array of sample containers and the aspirated sample is then dispensed from the probe into a remote injection port associated with an injection valve.

Although this type of known sample injection system has been quite successful, it is limited in throughput capabilities because of the use of a remote injection port that receives samples dispensed from the liquid handler probe. One difficulty is that sample cross contamination or carryover can occur as sequential samples are dispensed by the probe into the injector port. Such carryover decreases the accuracy of the sample analysis and results in loss of injection reproducibility. Although carryover can be reduced by sufficient intra sample rinsing, this adds to the time required to perform a series of sample injections and increases sample handling times and reduces sample throughput.

In a typical known system, the injection port into which samples are dispensed by the probe may be located as much as about two feet from certain ones of the liquid sample containers. Another difficulty is the time and the number of discrete operating steps needed for the liquid handler to move the probe into registration with each sample and then move the probe from the sample to the remote injection port. This also increases sample handling times and reduces sample throughput.

SUMMARY OF THE INVENTION

A primary object of the present invention is to provide a sample injection system having high sample throughput capability and increased injection repeatability but with minimal sample cross contamination carryover. Other objects are to provide a sample injection system in which the time and distance required for sample transfer are minimized and to provide a sample injection system that overcomes problems with known injection systems.

In brief, in accordance with the invention there is provided a sample injection system including a work surface for supporting a plurality of liquid sample containers and including a probe having a vertical axis. A probe drive system includes an X arm extending horizontally in an X direction, a Y arm slideably mounted on the X arm and extending horizontally in a Y direction, and a Z arm slideably mounted on the Y arm and extending vertically in Z direction. A probe holder holds the probe and is slideably mounted on the Z arm. A probe pump provides positive and negative pressure for the probe for sample dispensing and aspiration. The system includes a sample analyzer and a source of pressurized liquid phase. An injector valve is connected to the probe, to the probe pump, to the source of pressurized liquid phase and to the sample analyzer. A conduit connects the probe to the injector valve and the injector valve is mounted on the probe drive system.

BRIEF DESCRIPTION OF THE DRAWING

The present invention together with the above and other objects and advantages may best be understood from the following detailed description of the preferred embodiment of the invention illustrated in the drawings, wherein.

DETAILED DESCRIPTION OF THE PREFERRED EMBODIMENTS

Figure 1:
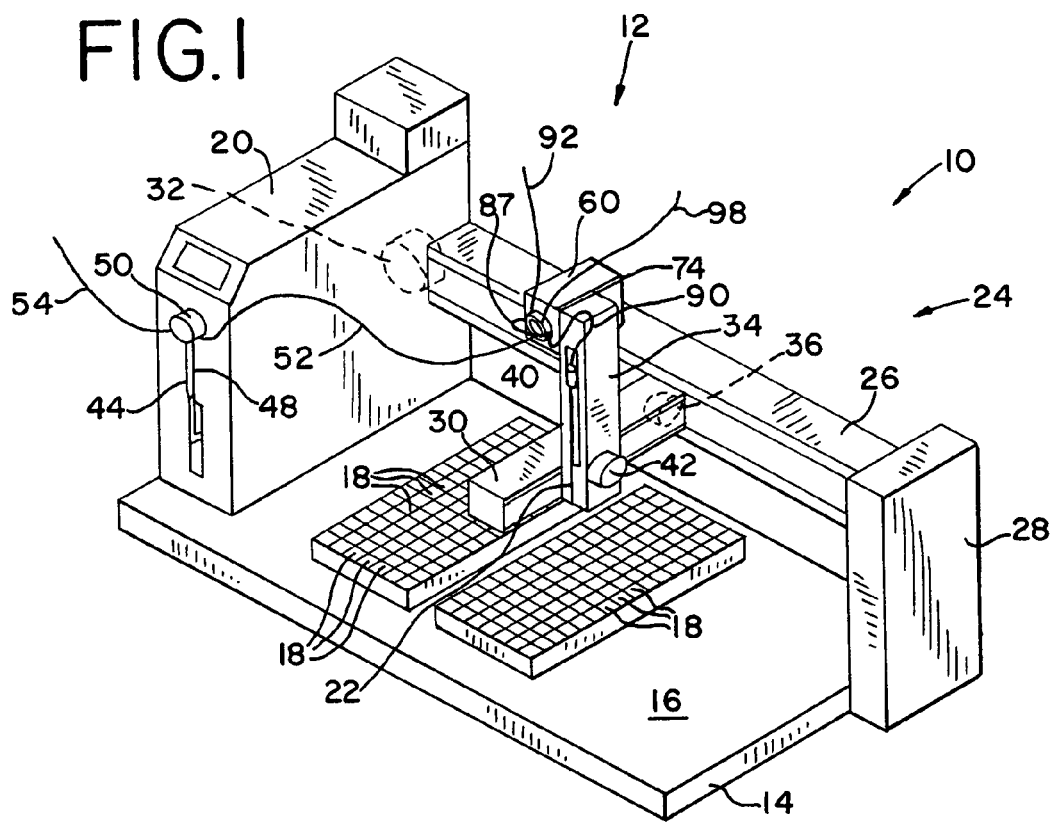
FIG. 1 is an isometric view of an automated liquid handler having a sample injection system constructed in accordance with the present invention.

Having reference now to FIG. 1 of the drawings, there is illustrated an automated liquid handler 10. The liquid handler 10 is provided with a sample injection system generally designated as 12 and constructed in accordance with the principles of the present invention.

The liquid handler 10 includes a base 14 providing a work surface 16 for locating and supporting an array of many sample containers or receptacles 18 in which liquid samples are held. The containers can take many forms, including microplates, test tubes and bottles. A control housing 20 is located at one end of the base 14. Liquid samples are aspirated from the containers 18 by a hollow probe 22 moved relative to the work surface 14 by a probe drive system 24.

The probe drive system is a three axis X-Y-Z drive system. An X arm 26 extends horizontally in an X direction and is supported along the rear of the work surface 16 between the upstanding control housing 20 and a support pedestal 28. A Y arm 30 extends horizontally in a Y direction from the X arm 26. The base of the Y arm 30 is slideably supported on the X arm for movement across the work surface 16 in the X direction. An X motor 32 is coupled to the Y arm and drives it in the X direction.

A Z arm 34 extends vertically in a Z direction from the Y arm 30. The base of the Z arm is slideably supported on the Y arm for movement in the Y direction across the work surface 16. A Y motor 36 is coupled to the Z arm and drives it in the Y direction. The X and Y motors 32 and 36 are operated by a controller 38 (FIGS. 3 and 4) within the control housing 20 in order to precisely position the probe 22 above any selected sample container 18.

The probe 22 is carried by a probe holder 40. The probe holder 40 is mounted on the Z arm 34 for vertical sliding movement. A Z motor 42 is coupled to the probe holder 40 and drives it in the vertical Z direction. When the probe 22 is aligned with a selected sample container 18, the Z motor 42 is operated by the controller 38 to lower the probe 22 into or raise the probe 22 upwardly from a liquid sample held in the sample container 18.

The automated liquid handler 10 may be of the construction disclosed in Gilson U.S. Pat. No. 4,422,151, incorporated herein by reference. The disclosure of that patent may be referred to for a description of the liquid handler 10 beyond that needed for an understanding of the present invention.

Figure 3:
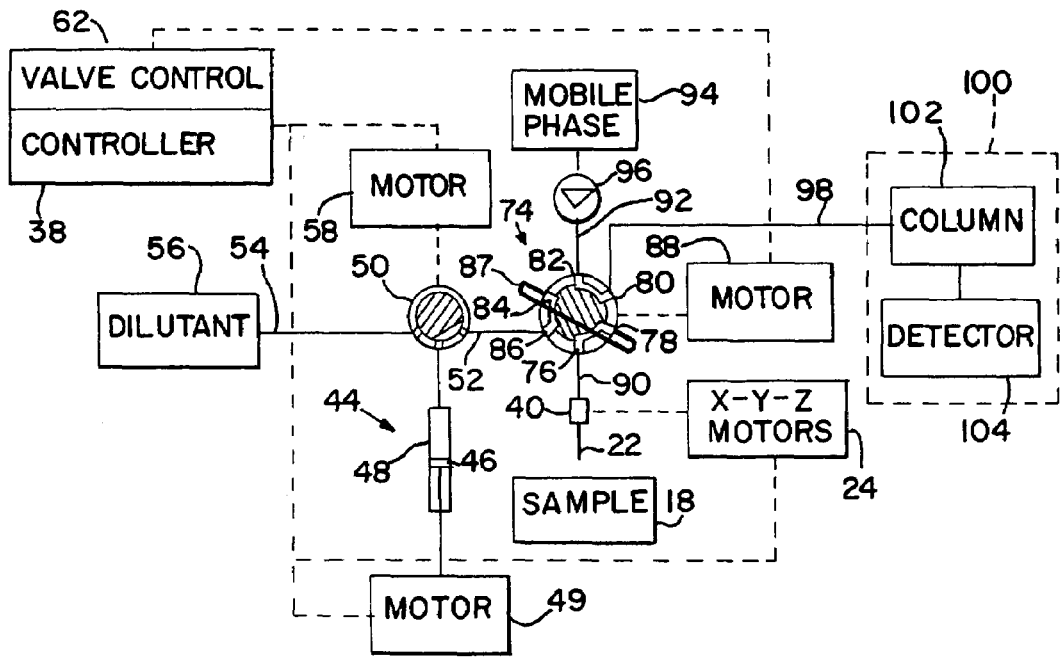
FIG. 3 is a schematic illustration of the sample injection system with the injection valve in the sample load position.
Figure 4:
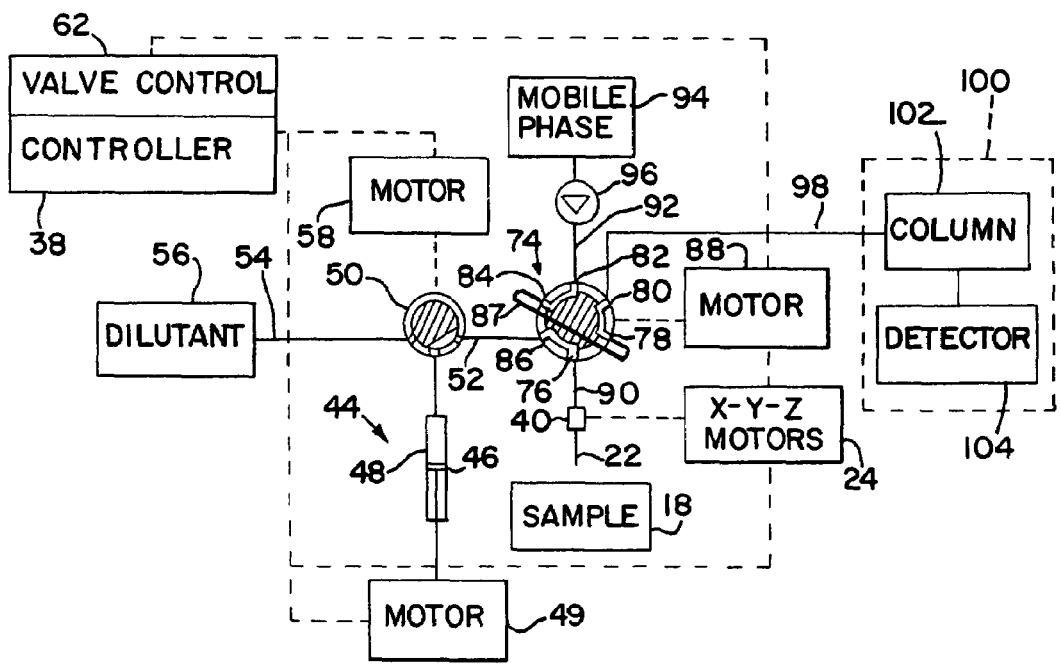
FIG. 4 is a schematic illustration of the sample injection system with the injection valve in the sample injection position.

A syringe probe pump 44 applies positive or negative pressure to the probe 22 for dispensing or aspirating liquid from or into the probe 22. The pump 44 includes a pump piston 46 moved within a cylinder 48 by a syringe pump motor 49 (FIGS. 3 and 4) located within the control housing 20 and operated by the controller 38. A three way syringe pump valve 50 is connected to the syringe pump 44 and is movable between one position in which the syringe pump 44 is able to communicate through a conduit 52 with the probe 22 and another position in which the syringe pump 44 communicates through a conduit 54 with a container 56 of dilutant or solvent (FIGS. 3 and 4). A syringe pump valve motor 58 (FIGS. 3 and 4) mounted within the control housing 20 operates the valve 50 between its alternate positions under the control of the controller 38.

Figure 2:
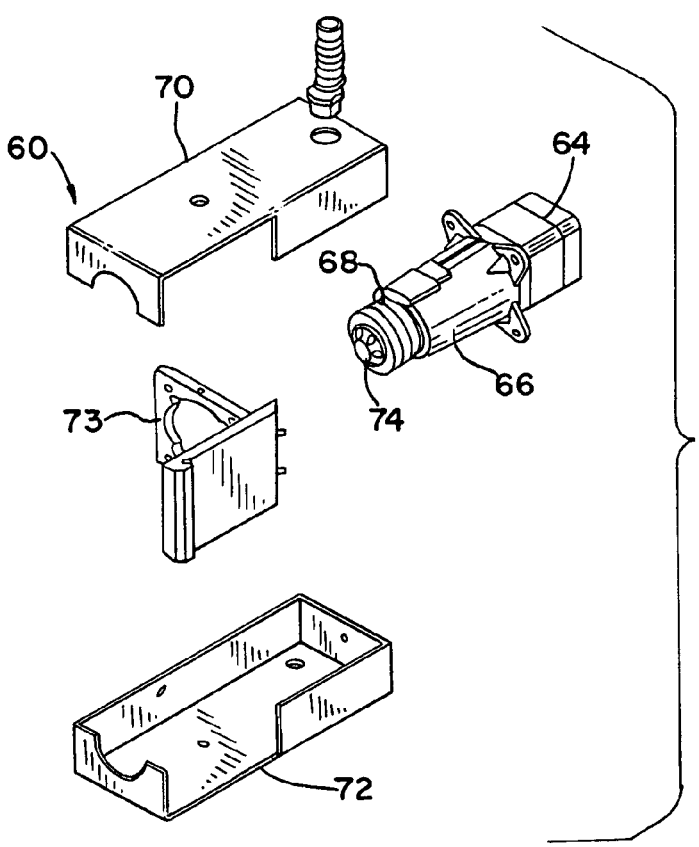
FIG. 2 is an exploded isometric view of the injection valve assembly of the sample injection system.

The sample injection system 12 includes an injection valve assembly 60 operated by an injection valve interface control module 62 in turn operated in accordance with operating instructions provided by the controller 38. As seen in FIG. 2, the injection valve assembly 60 includes a valve operating motor 64 and a bearing support body 66 supporting a valve head 68. These components are contained between upper and lower housing sections 70 and 72. An internal mounting flange 73 holds the valve components in the housing.

In the illustrated sample injection system 12, the valve head 68 includes a six port injection valve 74 having ports 76, 78, 80, 82, 84 and 86 (FIGS. 3 and 4). An external sample loop 87 is connected between injector valve ports 78 and 84. However the principles of the invention can be applied to other injector valve systems, such as four port injector valves having an internal sample loop. Under the control of the controller 38 and valve control 62, the injector valve is operated by a motor 88 between a sample loading position (FIG. 3) and an alternate sample injection position (FIG. 4). One commercially available injection valve suitable for use in the sample injection system 12 is a RHEODYNE™ RV700-100 injection valve sold by Rheodyne, L. P. Rohnert park, Calif. 94927.

The port 76 is connected to the probe 22 by a conduit 90. A conduit 92 connects port 82 to a source of pressurized mobile phase. In the illustrated system, mobile phase is supplied from a container 94 by a high pressure precision pump 96. One suitable pump is disclosed in Gilson et al. U.S. Pat. No. 4,326,837, incorporated herein by reference. The disclosure of that patent may be referred to for a description of the pump 96 beyond that needed for an understanding of the present invention. Port 80 is connected by a conduit 98 to a sample analyzer 100. Analyzers of many types could be used with the sample injection system 12. In the illustrated system, the analyzer includes a high pressure liquid chromatography (HPLC) column 102 communicating with a detector 104. The detector 104, for example, may be an ion detector, a mass spectrometer or other type.

In operation of the sample injection system 12, the injection valve 74 is placed by motor 88 into the sample loading position of FIG. 3. The probe drive system 24 positions the probe 22 over a selected sample container 18. The Z drive motor 42 lowers the probe into the selected liquid sample. The syringe pump valve 50 is in the position seen in FIGS. 3 and 4. The syringe pump 44 communicates with the probe 22 through a flow path including valve 50, conduit 52, injection valve port 86, the sample loop 87, injection valve port 76 and conduit 90. The syringe pump motor 49 operates to reduce pressure in the syringe pump 44 and liquid sample is aspirated through the probe 22 and into the sample loop 87. During the sample loading operation, mobile phase travels from the pump 94 through injection valve ports 82 and 80 toward the HPLC column 102.

The injection valve is then operated by motor 88 to the alternate, sample injection position of FIG. 4. Pressurized mobile phase from the pump 96 and conduit 92 enters injection valve port 82 and forces the liquid sample in sample loop 87 along a flow path including the sample loop 87, the injection valve port 80 and the conduit 98 toward the HPLC column 102. The liquid sample from the sample loop is thus entrained in the liquid phase for analysis in the analyzer 100. During the sample injection operation, the probe 22 is in communication with the syringe pump valve 50 through injection valve ports 76 and 86.

Prior to the next sample loading operation, the probe 22 and conduit 90 are preferably rinsed to reduce cross sample contamination carryover. The probe 22 can be moved to a rinsing station and rinsed with solvent, and/or the probe may be rinsed with solvent provided by valve 50 and the syringe pump 44 from the dilutant container 56.

In accordance with the invention, the injection valve 74 is mounted near the probe 22, and the probe 22 and the injection valve 74 are connected directly and continuously by the short conduit 90. The injection valve assembly 60 is attached to the drive system 24, and preferably to the Z arm 34 near the top of the Z arm. In this mounting position, the injector valve 74 is close to the vertical axis of the probe 22. The distance between the probe axis and the injector valve is only a few inches, preferably less than six inches. The conduit 90 is flexible to permit vertical motion of the probe 22. The short separation distance between the probe axis and the injection valve 74 permits the conduit 90 to be only several inches long, and preferably less than twelve inches long.

Because the probe 22 and injection port 76 are continuously interconnected by the conduit 90, it is not necessary for the probe to aspirate liquid sample from a sample container and then dispense the liquid sample into an injection port at a remote location. It is not necessary for the probe to be driven from a selected sample container to a remote injection port. Sample throughput rates are maximized and sample carryover is minimized. High injection reproducibility is achieved.

While the present invention has been described with reference to the details of the embodiment of the invention shown in the drawing, these details are not intended to limit the scope of the invention as claimed in the appended claims.

What is claimed is:

1. A liquid chromatography sample injection system comprising: an arm;
    a probe mounted on the arm;
    an injector valve mounted on the arm;
    a conduit, wherein the conduit directly connects the injector valve and the probe;
    a source of dilutant;
    a probe pump;
    a pump valve interfacing with the injector valve, the probe pump and the source of dilutant; and
    a controller operably coupled to the probe pump, the injector valve, and the pump valve, wherein the controller alternates the injector valve between a loading position and an injection position and alternates the pump valve between a first position where a sample can be aspirated and dispensed through the probe and a second position where the probe can be rinsed via communication between the probe pump and the source of dilutant after the injector valve loads the sample and injects the sample.

2. The liquid chromatography sample injection system of claim 1, further comprising a source of mobile phase interfacing with the injector valve.

3. The liquid chromatography sample injection system of claim 2, wherein a high pressure pump supplies the mobile phase from the source of mobile phase to the injector valve.

4. The liquid chromatography sample injection system of claim 1, further comprising a sample analyzer interfacing with the injector valve.

5. The liquid chromatography sample injection system of claim 2, wherein the mobile phase comprises a pressurized liquid phase.

6. The liquid chromatography sample injection system of claim, 4 wherein the sample analyzer comprises a liquid chromatography column.

7. The liquid chromatography sample injection system of claim 6, wherein the sample analyzer further comprises a detector.

8. The liquid chromatography sample injection system of claim 7, wherein the detector comprises an ion detector or a mass spectrometer.

9. The liquid chromatography sample injection system of claim 1, wherein the pump valve comprises a three-way valve.

10. The liquid chromatography sample injection system of claim 1, further comprising a probe drive system, wherein the probe drive system positions the arm.

11. The liquid chromatography sample injection system of claim 10, wherein the arm is part of a probe drive system, the probe drive system comprising an X arm extending horizontally in an X direction; a Y arm slidably mounted on the X arm wherein the Y arm extends horizontally in a Y direction and slides in the X direction; and a Z arm slidably mounted on the Y arm wherein the Z arm extends vertically in a Z direction and slides in the Y direction, and further wherein the arm on which the probe is mounted is the Z arm.

12. The liquid chromatography sample injection system of claim 1, wherein the injector valve is located within about 6 inches of a vertical axis of the probe.

13. The liquid chromatography sample injection system of claim 1 wherein the conduit has a length of less than 12 inches.

14. The liquid chromatography sample injection system of claim 4 wherein the mobile phase forces the sample toward the sample analyzer when the controller alternates the injector valve into the injection position.

15. The liquid chromatography sample injection system of claim 14 further comprising a motor, wherein the motor powers the alternation of the injector valve.

16. The liquid chromatography sample injection system of claim 1 wherein the injector valve is a six port injection valve.

17. The liquid chromatography sample injection system of claim 1 wherein the injector valve is a four port injector valve.

18. The liquid chromatography sample injection system of claim 10, wherein the arm is part of a probe drive system, and further wherein the controller operates the probe drive system.

19. A liquid handler comprising:
(a) a probe drive system; wherein the probe drive system comprises an X arm extending horizontally in an X direction; a Y arm slidably mounted on the X arm to move in the direction of the X arm wherein the Y arm extends horizontally in a Y direction; and a Z arm slidably mounted on the Y arm to move in the direction of the Y arm wherein the Z arm extends vertically in a Z direction; and a probe holder slidably mounted on the Z arm to move in the direction of the Z arm;
(b) an injector valve mounted on the Z arm of the probe drive system; wherein the injector valve comprises a sample loop, a probe port, a mobile phase input port, a column output port and a probe pump port;
(c) a probe connected to the probe port and the probe holder;
(d) a sample analyzer connected to the column output port;
(e) a probe pump connected to the probe pump port;
(f) a source of pressurized mobile phase connected to the mobile phase input port;
(g) a pump valve interfacing with the injector valve;
(h) a source of dilutant interfacing with the pump valve; and
(I) a controller, wherein the controller moves the pump valve wherein the pump valve is movable between a first position where the probe pump is operable to dispense and to aspirate a sample through the probe, and a second position where the probe pump communicates with the source of dilutant for rinsing the probe after the injector valve loads the sample and injects the sample toward the sample analyzer.

20. A method of injecting a sample into a sample analyzer of a liquid chromatography sample injection system comprising:
(a) placing an injection valve into a sample loading position, wherein the injection valve is mounted on an arm of a probe drive system of an automated liquid handler;
(b) operating a pump to provide a negative pressure through a pump valve to aspirate a liquid sample through a probe mounted on the arm of the probe drive system and into the injection valve;
(c) placing the injection valve into a sample injection position;
(d) entraining the liquid sample in the injection valve by addition of a mobile phase to force the liquid sample toward a sample analyzer;
(e) placing a pump valve into a rinse position automatically using a controller after forcing the liquid sample toward the sample analyzer; and
(f) rinsing the probe by operating the pump to deliver a solvent through the pump valve and the injection valve to the probe.

* * * * *